United States Patent
Ebina et al.

(10) Patent No.: US 12,317,404 B2
(45) Date of Patent: May 27, 2025

(54) CIRCULAR ACCELERATOR AND PARTICLE THERAPY SYSTEM

(71) Applicant: Hitachi High-Tech Corporation, Tokyo (JP)

(72) Inventors: Futaro Ebina, Tokyo (JP); Takuya Nomura, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 41 days.

(21) Appl. No.: 17/953,369

(22) Filed: Sep. 27, 2022

(65) Prior Publication Data
US 2023/0180378 A1 Jun. 8, 2023

(30) Foreign Application Priority Data
Dec. 8, 2021 (JP) .................................. 2021-199071

(51) Int. Cl.
*H05H 13/00* (2006.01)
*A61N 5/10* (2006.01)
(Continued)

(52) U.S. Cl.
CPC ................. *H05H 7/04* (2013.01); *A61N 5/10* (2013.01); *H05H 7/001* (2013.01); *H05H 7/10* (2013.01);
(Continued)

(58) Field of Classification Search
CPC ............ H05H 7/04; H05H 7/001; H05H 7/10; H05H 13/005; H05H 13/04;
(Continued)

(56) References Cited

U.S. PATENT DOCUMENTS 9,757,590 B2 * 9/2017 Hiramoto ............. A61N 5/1081
10,485,995 B2 * 11/2019 Anferov ............... A61N 5/1077
(Continued)

FOREIGN PATENT DOCUMENTS

JP      6-338400 A    12/1994
JP      4115468 B2    7/2008
(Continued)

OTHER PUBLICATIONS

Extended European Search Report received in corresponding European Application No. 22209625.7 dated Sep. 25, 2023.
(Continued)

*Primary Examiner* — Tuan T Lam
(74) *Attorney, Agent, or Firm* — MATTINGLY & MALUR, PC

(57) ABSTRACT

There is provided a circular accelerator that accelerates a beam of charged particles circulating in a magnetic field such that a closed orbit for each energy of the beam is eccentric. The circular accelerator includes a beam extraction port for extracting beams of different energies from the closed orbit, a first bending magnet and a second bending magnet that bend the beam extracted from the beam extraction port, and a control unit that controls magnetic field strengths of the first bending magnet and the second bending magnet in accordance with the energy of the extracted beam. When the energy of the extracted beam is a designed maximum energy of the circular accelerator, the control unit excites both the first bending magnet and the second bending magnet to bend the beam.

10 Claims, 4 Drawing Sheets

(51) Int. Cl.
   *H05H 7/00* (2006.01)
   *H05H 7/04* (2006.01)
   *H05H 7/10* (2006.01)
   *H05H 13/04* (2006.01)

(52) U.S. Cl.
   CPC ............... *A61N 2005/1085* (2013.01); *H05H 2007/002* (2013.01); *H05H 2007/008* (2013.01); *H05H 2007/045* (2013.01); *H05H 13/005* (2013.01); *H05H 13/04* (2013.01); *H05H 2277/11* (2013.01)

(58) Field of Classification Search
   CPC ....... H05H 2007/002; H05H 2007/008; H05H 2007/045; H05H 2277/11; H05H 13/00; A61N 5/10; A61N 2005/1085
   See application file for complete search history.

(56) References Cited

U.S. PATENT DOCUMENTS

| | | | |
|---|---|---|---|
| 10,864,384 B2* | 12/2020 | Huggins | A61N 5/1081 |
| 2004/0227104 A1* | 11/2004 | Matsuda | G21K 1/08 |
| | | | 250/492.1 |
| 2006/0145088 A1 | 7/2006 | Ma | |
| 2009/0289194 A1* | 11/2009 | Saito | H05H 7/04 |
| | | | 250/492.1 |
| 2016/0136461 A1* | 5/2016 | Iwata | A61N 5/1079 |
| | | | 600/1 |
| 2017/0303384 A1 | 10/2017 | Aoki et al. | |
| 2019/0239333 A1 | 8/2019 | Aoki | |
| 2021/0195725 A1 | 6/2021 | Hae et al. | |

FOREIGN PATENT DOCUMENTS

| | | |
|---|---|---|
| JP | 2019-133745 A | 8/2019 |
| WO | 2019/093110 A1 | 5/2019 |

OTHER PUBLICATIONS

Botha, A. H., "The Status of the South African National Accelerator Centre", IEEE Transactions on Nuclear Science, Apr. 1979, pp. 1896-1903.
Calabretta, A. et al., "New Extraction Line for the LNS Cyclotron", Proceedings of the IPAC 2017, 2017, pp. 3378-3380.
Smirnov, V. et al., "Superconducting 70 AmeV cyclotron-injector for a hadron therapy complex", Nuclear Instruments & Methods in Physics Research, 2019, pp. 1-9.
Berg, R. E., "Design of the beam transport system for the university of Maryland cyclotron", IEEE Transations on Nuclear Science, 1969, pp. 442-445.
Herminghaus, H., "The polytron as a CW electron accelerator in the 10 GeV range", Nuclear Instruments in Physics, Jul. 10, 1991, pp. 1-9.
Vorobiev, L. G., "Concepts of a compact achromatic proton gantry with a wide scanning field", Nuclear Instruments and Methods in Physics Research, 1998, pp. 307-310.
Pavlovic, M. et al., "Beam-transport study of an isocentric rotating ion gantry with minimum number of quadrupoles", Nuclear Instruments and Methods in Physics Research, 2005, pp. 412-426.
Maradia, V. et al., "A new emittance selection system to maximize beam transmission for low-energy beams in cyclotron-based proton therapy facilities with gantry", Medical Physics, Aug. 24, 2021, pp. 7613-7622.
Schippers, J. M., "Beam-Transport Systems for Particle Therapy", Cornell University Library, 2018.
Japanese Office Action received in corresponding Japanese Application No. 2021-199071 dated Nov. 12, 2024.

* cited by examiner

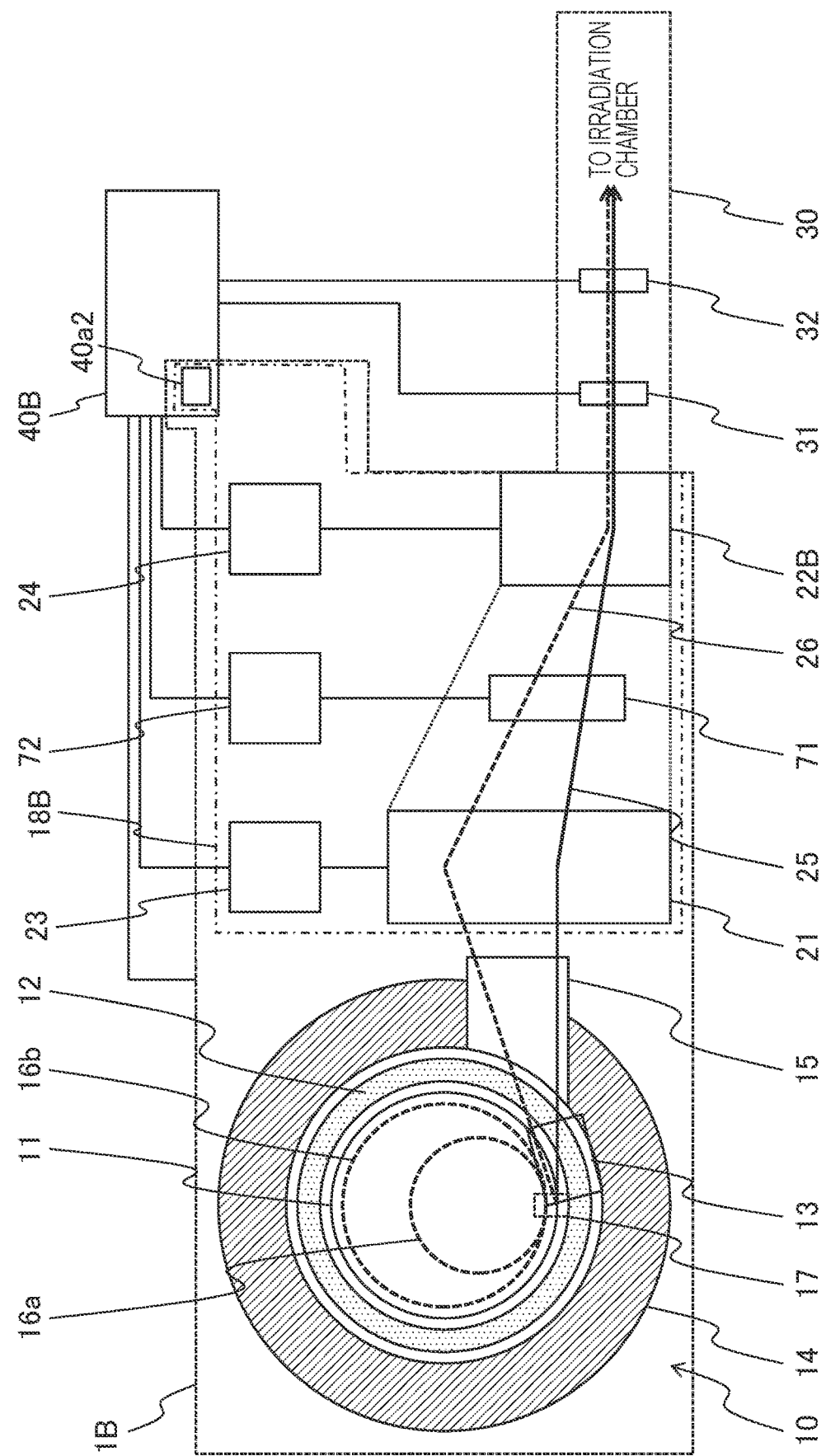

CIRCULAR ACCELERATOR AND PARTICLE THERAPY SYSTEM

CROSS-REFERENCE TO RELATED APPLICATION

The present application claims priority from Japanese application JP2021-199071, filed on Dec. 8, 2021, the contents of which is hereby incorporated by reference into this application.

BACKGROUND OF THE INVENTION

1. Field of the Invention

The present invention relates to a circular accelerator that accelerates a particle beam, and a particle therapy system.

2. Description of the Related Art

As an example of a technique for controlling extraction of a charged particle beam from a circular accelerator with high accuracy in the circular accelerator that accelerates a charged particle beam while increasing an orbital radius, by feeding a radio frequency in a main magnetic field, JP 2019-133745 A discloses that a charged particle beam is extracted by feeding a radio frequency having a frequency different from that of a radio frequency used for acceleration to the charged particle beam in a circular accelerator that accelerates the charged particle beam while increasing an orbital radius by feeding the radio frequency in a main magnetic field.

JP 4115468 B2 is an example of a particle therapy system in which the adjustment time of a particle accelerator is reduced, the number of types of operation parameter files is small, the movement sound and the energy change time of a range shifter can be greatly reduced, the frequency of the system stop due to the device fluctuation of the particle accelerator is low, and the fluctuation in the energy and the intensity of the charged particle beam is small. JP 4115468 B2 discloses a particle therapy system including an energy change apparatus that includes a range shifter, an upstream bending magnet pair, a downstream bending magnet pair, and a change control apparatus. In the range shifter, the thickness in a direction in which a charged particle beam is transmitted is different from one direction perpendicular to a beam transmission direction, and the energy of the transmitted charged particle beam is decreased by an amount proportional to the thickness. The upstream bending magnet pair translates the orbit of the charged particle beam in a direction in which the thickness changes on the upstream side of the range shifter in order to transmit the charged particle beam to a portion having a different thickness in the range shifter. The downstream bending magnet pair translates the orbit of the charged particle beam transmitted through the range shifter, onto an extension line of an orbit when the charged particle beam is injected to the upstream bending magnet pair. The change control apparatus controls the upstream bending magnet pair and the downstream bending magnet pair such that the charged particle beam travels on an orbit in which the energy of the charged particle beam is reduced to a desired value by transmitting the charged particle beam through the range shifter.

SUMMARY OF THE INVENTION

A particle therapy in which a charged particle beam (simply referred to as a beam below) is accelerated by an accelerator such as a synchrotron or a cyclotron, and a lesion such as a cancer is irradiated with the accelerated beam is performed.

As one type of accelerator used in the particle therapy, for example, there is an accelerator as disclosed in JP 2019-133745 A. In the circular accelerator disclosed in JP 2019-133745 A, a circular closed orbit (referred to as a center orbit below) formed by beam particles having different kinetic energies (simply referred to as energy below) in a static magnetic field is disposed to be eccentric toward an extraction port of a beam from the accelerator, and beams having different energies are extracted from the same beam extraction port to the outside of the accelerator.

In the circular accelerator disclosed in JP 2019-133745 A, a beam (referred to as a circulating beam below) circulating in the accelerator is accelerated to a desired energy, and then a radiofrequency voltage in a direction (referred to as a horizontal direction below) perpendicular to a beam traveling direction and a magnetic pole gap direction (referred to as a vertical direction below) is fed to the circulating beam. The beam particles to which the radiofrequency voltage is fed gradually increase the horizontal amplitude of oscillation (referred to as betatron oscillation below) about the center orbit, and comes into contact with a magnetic field distribution for generating the resonance of the betatron oscillation, which is called a peeler magnetic field and a regenerator magnetic field formed around the center orbit. The beam particles in contact with the peeler magnetic field and the regenerator magnetic field rapidly increase in the horizontal amplitude of the betatron oscillation, and are injected to a septum coil for extraction. The septum coil bends the beam in an outer circumferential direction of the circular accelerator. The bent beam is extracted into high energy beam transport that is on the outside of the circular accelerator.

Thus, the circular accelerator disclosed in JP 2019-133745 A is a circular accelerator that accelerates a beam in a static magnetic field, and can switch the energy of a beam extracted from the circular accelerator in a predetermined range (for example, a range of 70 MeV to 230 MeV).

On the other hand, in the circular accelerator disclosed in JP 2019-133745 A, the septum coil is installed in a limited space in the magnetic pole of the circular accelerator. Thus, the strength of the magnetic field (septum magnetic field) generated by the septum coil is limited. The septum coil has a function of aligning the orbits of beams having different energies at the extraction port of the circular accelerator. Thus, in the circular accelerator disclosed in JP 2019-133745 A, there is a possibility that the orbit of the beam extracted from the circular accelerator changes with the change in energy due to the shortage of the septum magnetic field.

Here, devices such as a bending magnet and a quadrupole magnet constituting the high energy beam transport need to be manufactured so as to include the beam orbits of all the energies passing through the high energy beam transport.

Therefore, in the circular accelerator disclosed in JP 2019-133745 A, in order to cope with the change in the orbit of the extracted beam, the constituent device of the high energy beam transport may be increased in size, and the installation area and cost of the high energy beam transport and an accelerator system constituted by the circular accelerator and the beam transport system are increased. Therefore, there is room for improvement.

The energy change apparatus disclosed in JP 4115468 B2 includes an energy absorber (range shifter) having different thicknesses depending on locations in a vertical plane to the beam orbit, two bending magnets installed on the upstream side of the range shifter, and two bending magnets installed on the downstream side of the range shifter.

In the energy change apparatus disclosed in JP 4115468 B2, the beam extracted from the accelerator is bent by the bending magnet on the upstream side to control the position at which the beam is injected to the range shifter, that is, the thickness of the range shifter. In addition, the energy of the beam after passing through the range shifter is changed to a desired value. The beam that has passed through the range shifter is bent by the bending magnet on the downstream side, and then is aligned on an extension line of the beam orbit before being injected to the energy change apparatus. As a result, the energy change apparatus disclosed in JP 4115468 B2 can adjust the energy of the beam to a desired value without changing the orbit of the beam. Thus, it is possible to adjust the energy of the beam extracted from a static magnetic field type accelerator such as a cyclotron and to be used for applications such as particle therapy.

On the other hand, since the energy change apparatus disclosed in JP 4115468 B2 uses the range shifter to change the energy, the spatial spread (beam size) of the beam after the energy change may be expanded due to scattering between the beam and the range shifter.

In recent years, in particle therapy, a scanning irradiation method of three-dimensionally scanning a target volume with a small-diameter beam has become widespread, and it is desirable to suppress an increase in beam size as much as possible in order to form a highly accurate dose distribution by the scanning irradiation method.

Therefore, in the case using the energy change apparatus disclosed in JP 4115468 B2, when the beam passes through the range shifter, the spread (referred to as the momentum variance below) of the energy of the beam particles may be expanded, the passing efficiency of the high energy beam transport may be lowered, and the effective beam current may be reduced. Therefore, it is difficult to apply the technique itself, and improvement is required.

The present invention has been made in view of the above problems, and an object of the present invention is to provide a circular accelerator and a particle therapy system capable of performing irradiation with a beam having a high current and high quality at low cost.

The present invention includes a plurality of means for solving the above problems. An example thereof is a circular accelerator that accelerates a beam of charged particles circulating in a magnetic field such that a closed orbit for each energy of the beam is eccentric. The circular accelerator includes a beam extraction port for extracting beams of different energies from the closed orbit, a first bending magnet and a second bending magnet that bend the beam extracted from the beam extraction port, and a control unit that controls magnetic field strengths of the first bending magnet and the second bending magnet in accordance with the energy of the extracted beam. When the energy of the extracted beam is a designed maximum energy of the circular accelerator, the control unit excites both the first bending magnet and the second bending magnet to bend the beam.

According to the present invention, it is possible to provide a circular accelerator and a particle therapy system capable of performing irradiation with a beam having a high current and high quality at low cost. Objects, configurations, and advantageous effects other than those described above will be clarified by the descriptions of the following embodiments.

BRIEF DESCRIPTION OF THE DRAWINGS

FIG. 4 is a schematic diagram illustrating a configuration of a circular accelerator according to a third embodiment of the present invention.

DESCRIPTION OF THE PREFERRED EMBODIMENTS

Figure 1:
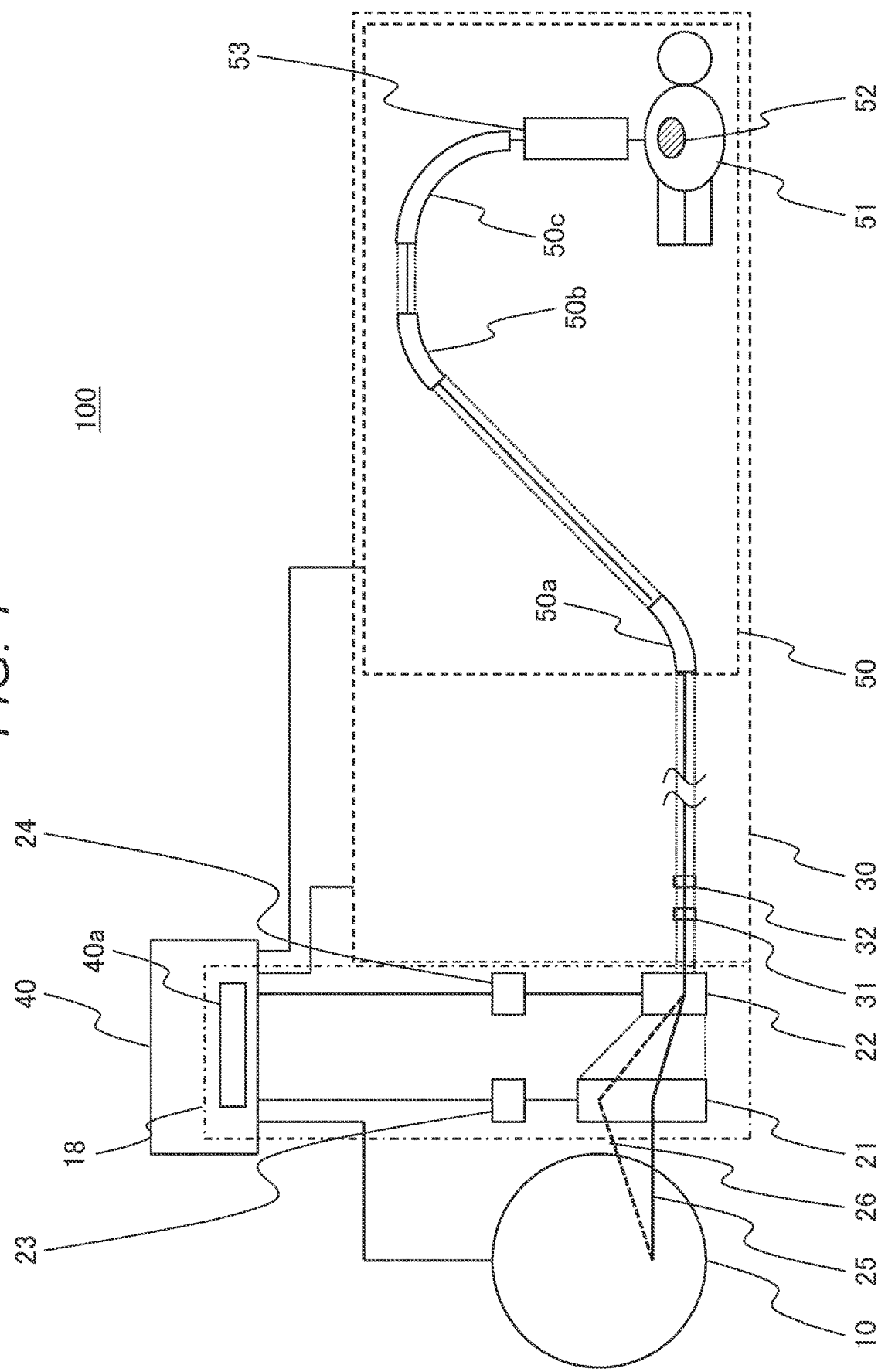
FIG. 1 is a schematic diagram illustrating a configuration of a particle therapy system using a circular accelerator according to a first embodiment of the present invention.

Hereinafter, a circular accelerator and a particle therapy system according to embodiments of the present invention will be described with reference to the drawings. In the drawings used in the present specification, the same or corresponding components are denoted by the same or similar reference signs, and repeated description of the components may be omitted.

First Embodiment

A circular accelerator and a particle therapy system according to a first embodiment of the present invention will be described with reference to FIGS. 1 and 2.

First, an overall configuration of a particle therapy system including a circular accelerator will be described with reference to FIG. 1. FIG. 1 is a schematic diagram illustrating the configuration of the particle therapy system using the circular accelerator according to the first embodiment.

A particle therapy system 100 in the present embodiment illustrated in FIG. 1 includes a circular accelerator 1, a high energy beam transport 30, an irradiation nozzle 53, a control apparatus 40, and the like. The circular accelerator 1 accelerates and extracts a beam of charged particles circulating in a magnetic field. The high energy beam transport 30 transports a charged particle beam accelerated by the circular accelerator 1. The irradiation nozzle 53 is provided for performing irradiation with the charged particle beam transported by the high energy beam transport 30.

In the particle therapy system 100, the high energy beam transport 30 transports the beam extracted from the circular accelerator 1 and a target volume 52 of a patient 51 is irradiated with the transported beam. In this manner, a lesion such as cancer is treated.

A rotating gantry 50 is provided at a rear stage of the high energy beam transport 30. The rotating gantry 50 rotates around the patient 51 to enable beam irradiation from a plurality of different directions.

The irradiation nozzle 53 that shapes the beam from the circular accelerator 1 with matching with the shape of the target volume 52 is provided in the most downstream straight line portion of the rotating gantry 50.

Devices such as electromagnets constituting the high energy beam transport 30 and the rotating gantry 50 are connected to the control apparatus 40, similar to the circular accelerator 1.

In the particle therapy, a distance (referred to as a range below) at which the beam travels inside the body of the patient 51 is controlled by the energy of the beam with which the patient 51 is irradiated.

The control apparatus 40 controls the circular accelerator 1 based on information (referred to as treatment planning below) on an irradiation point and an irradiation dose of the beam, which has been created in advance for each patient 51. In addition, the control apparatus 40 adjusts the energy of the beam extracted from the circular accelerator 1, to a value corresponding to the depth of the target volume 52. The control apparatus 40 controls a first bending magnet 21, a second bending magnet 22, the high energy beam transport 30, and the rotating gantry 50 based on the treatment planning. The target volume 52 is irradiated with the beam extracted from the circular accelerator 1.

Next, the configuration of the circular accelerator will be described with reference to FIG. 2. FIG. 2 is a schematic diagram illustrating an outline of the circular accelerator 1 in the present embodiment, in particular, a beam orbit adjustment device provided outside the main body 10 of the circular accelerator 1.

Figure 2:
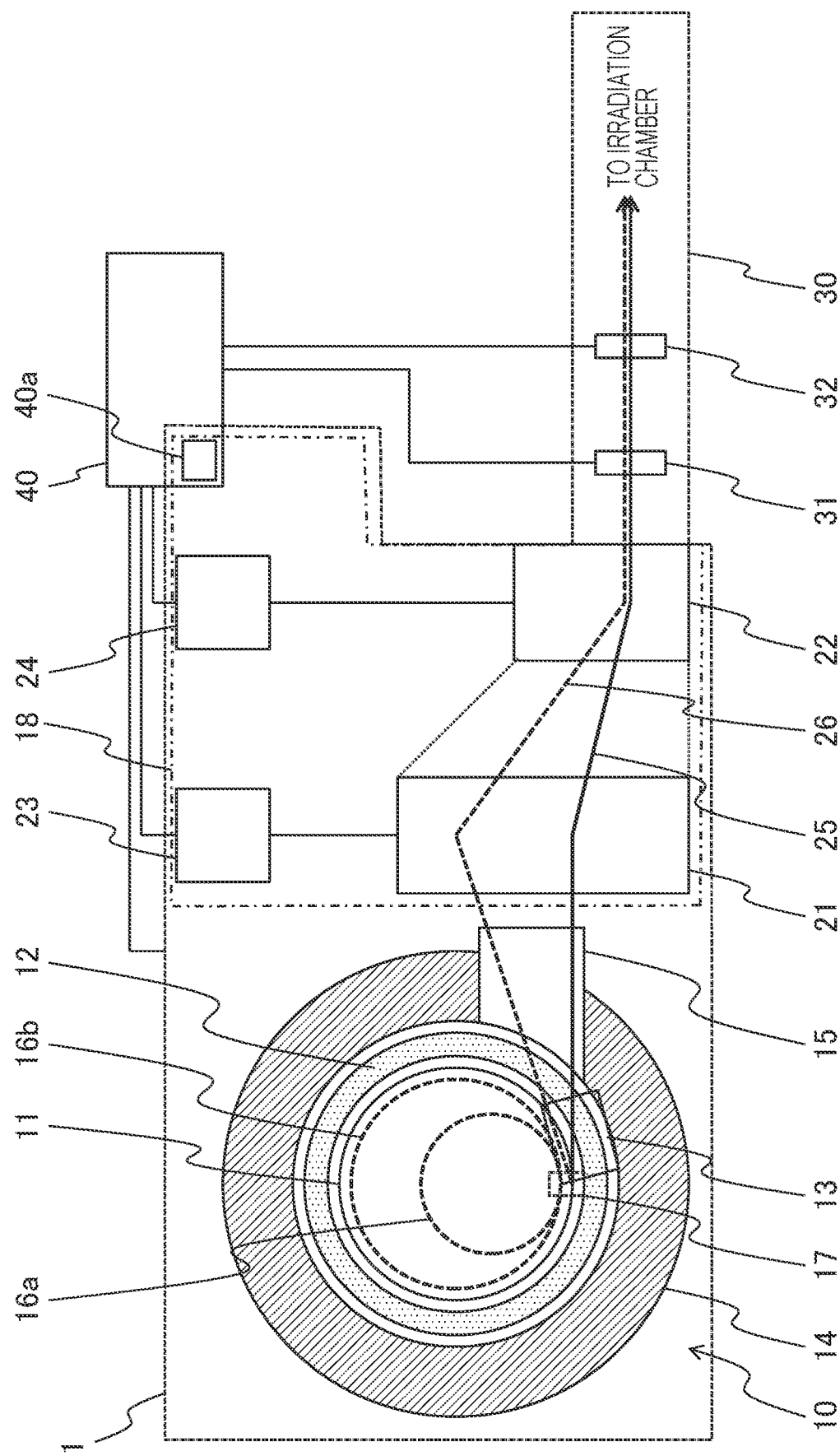
FIG. 2 is a schematic diagram illustrating a configuration of the circular accelerator according to the first embodiment.

As illustrated in FIG. 2, the circular accelerator 1 includes a magnetic pole 11, a coil 12, an extraction magnetic field generator 13, and a yoke 14. An extraction port 15 of a beam is formed in the yoke 14. When a predetermined current flows through the coil 12, a magnetic field (referred to as a main magnetic field below) for circulating the beam in the circular accelerator 1 is generated between the magnetic poles 11, and thus a circular circulating beam orbit 16 is formed on an orbit plane. The radius of the circulating beam orbit 16 increases as the kinetic energy (simply referred to as the energy below) of the beam particle increases.

In the circular accelerator 1 in the present embodiment, the closed orbit for each energy of the beam is eccentric. More specifically, the center of the circulating beam orbit 16 becomes farther from the extraction magnetic field generator 13 as the energy increases. An orbit aggregation region 17 in which the circulating beam orbits 16 having different energies converge in a narrow region is formed in the vicinity of the extraction magnetic field generator 13. By forming the orbit aggregation region 17, the circular accelerator 1 can extract beams having different energies from the common extraction port 15 without changing the strength of the main magnetic field.

The extraction magnetic field generator 13 bends the beam injected to the extraction magnetic field generator 13 and guides the beam to the extraction port 15. The extraction magnetic field generator 13 includes, for example, a septum coil formed along the beam orbit. The septum coil has a configuration in which a direction and an amount of bending a beam can be adjusted in accordance with the energy by changing a current flowing through the coil. In the present embodiment, an example in which the extraction magnetic field generator 13 includes the septum coil has been described. A configuration in which a magnetic field correction structural member (referred to as a magnetic channel below) configured of a magnetic body such as iron is disposed along the beam orbit instead of the septum coil may be made. The magnetic channel does not require a power supply for excitation, but the generated magnetic field is constant regardless of the energy of the beam. The extraction magnetic field generator 13 may be configured by disposing both the septum coil and the magnetic channel.

The first bending magnet 21 and the second bending magnet 22 are installed on the downstream side of the extraction port 15 of the circular accelerator 1. An orbit control apparatus 18 in the present embodiment includes the first bending magnet 21, the second bending magnet 22, power supplies 23 and 24, and a control unit 40a (preferably, a portion of the control apparatus 40). The first bending magnet 21 is connected to the power supply 23, and the second bending magnet 22 is connected to the power supply 24. The control unit 40a controls the power supply 23 to control an excitation current for excitation in the first bending magnet 21. In addition, the control unit 40a controls the power supply 24 to control an excitation current for excitation in the second bending magnet 22.

The first bending magnet 21 bends the beam in a direction away from the center of the magnetic pole 11, that is, in the outer circumferential direction of the circular accelerator 1. The second bending magnet 22 bends the beam in a direction approaching the center of the magnetic pole 11, that is, in the inner circumferential direction of the circular accelerator 1.

In the present embodiment, as illustrated in FIG. 1, the diameter of the first bending magnet 21 is greater than the diameter of the second bending magnet 22 and the diameters of bending magnets 50a, 50b, and 50c constituting the high energy beam transport 30.

As illustrated in FIG. 1, the second bending magnet 22 is smaller in diameter than the first bending magnet 21, but is greater in diameter than the bending magnets 50a, 50b, and 50c constituting the high energy beam transport 30. The diameter of the second bending magnet 22 is not necessarily smaller than the diameter of the first bending magnet 21 and greater than the diameters of the bending magnets 50a, 50b, and 50c. The diameter of the second bending magnet 22 may be equal to the diameter of the first bending magnet 21 or equal to the diameters of the bending magnets 50a, 50b, and 50c. When the diameter of the second bending magnet 22 is equal to the diameter of the first bending magnet 21 or the diameters of the bending magnets 50a, 50b, and 50c, specifications thereof are made common. Therefore, it is not necessary to manufacture the second bending magnet as a bending magnet having a dedicated specification, and thus it is possible to reduce the cost.

The diameter of a vacuum duct (not illustrated for convenience of illustration) disposed inside the bending magnet tends to be equal to the diameter of the bending magnet. For example, the diameter of the vacuum duct in a portion at which the first bending magnet 21 is installed is greater than the diameter of the vacuum duct in a portion at which the second bending magnet 22 is installed and the diameter of the vacuum duct in a portion at which the bending magnets 50a, 50b, and 50c are installed.

The high energy beam transport 30 that transports a beam to an irradiation target is formed on the downstream side of the second bending magnet 22. Profile monitors 31 and 32 that measure the position and the shape of the beam in a vertical plane to a beam traveling direction are installed in a straight line portion immediately after the second bending magnet 22 in the high energy beam transport 30. The installation locations of the profile monitors that measure the position and the shape of the beam is not limited to locations in the high energy beam transport 30, and the profile monitors may be provided at other locations, for example, in the orbit control apparatus 18.

The first bending magnet 21 is connected to the power supply 23, and the second bending magnet 22 is connected to the power supply 24. The power supply 23, the power supply 24, the circular accelerator 1, and the profile monitor 31 are connected to the control apparatus 40.

A method for providing an accelerator system capable of performing irradiation with a beam having a high current and high quality at low cost by the circular accelerator 1 in the present embodiment will be described.

The circular accelerator 1 in the present embodiment can extract beams having different energies from the common extraction port 15 without changing the strength of the main magnetic field. However, the orbit of the beam at the extraction port 15 may be different for each energy within a range in which the beam can pass through the extraction port 15.

The cause of the beam orbit deviation at the extraction port 15 is, for example, that it is not possible for the septum coil constituting the extraction magnetic field generator 13 to generate a magnetic field having sufficient strength, and that the magnetic field generated by a magnetic channel is constant regardless of the energy. How much the magnetic field strength of the septum coil is insufficient depends on the design of the circular accelerator 1. When a main magnetic field (for example, about 2.5 T) having high strength is generated for the purpose of reducing the size of the circular accelerator 1, the magnetic field strength of the septum coil is insufficient, which is a problem.

In addition, when the extraction magnetic field generator 13 is configured by a magnetic channel, the beam orbit at the extraction port 15 changes depending on the energy regardless of the design of the circular accelerator 1.

When the high energy beam transport is connected immediately after the extraction port 15, the constituent devices of the high energy beam transport 30, for example, electromagnets such as the bending magnets 50a, 50b, and 50c and quadrupole magnets, and measurement devices such as the profile monitors 31 and 32 need to be designed to be large so that beams of all energies can pass through the insides thereof. As a result, in the accelerator system using the conventional circular accelerator, the installation area and the manufacturing cost of the high energy beam transport may increase.

Therefore, in the circular accelerator 1 in the present embodiment, the first bending magnet 21 and the second bending magnet 22 are installed on the downstream side of the extraction port 15, and the magnetic field strengths of the first bending magnet 21 and the second bending magnet 22 are controlled so that the orbits of beams having different energies coincide with each other on the downstream side of the second bending magnet 22. Thus, in the circular accelerator 1 in the present embodiment, it is possible to realize prevention of the expansion of a beam passage region in the high energy beam transport 30 and suppression of the size of the device constituting the high energy beam transport 30.

The magnetic field strength of an electromagnet represents the strength of the magnetic field generated by the electromagnet, and is generally proportional to a current flowing through a coil constituting the electromagnet. The power supply 23 controls a current flowing through the coil of the first bending magnet 21. The power supply 24 controls a current flowing through the coil of the second bending magnet 22.

Next, a method of causing the orbits of beams having different energies in the high energy beam transport 30 to coincide with each other by using the first bending magnet 21 and the second bending magnet 22 will be described.

A magnetic field that bends the beam toward the inner circumferential side of the circular accelerator 1 is generated inside the circular accelerator 1. Thus, the orbit of the beam having higher energy is located on the outer peripheral side at the extraction port 15, and the orbit is different for each energy.

In FIG. 2, an orbit 25 represents a designed beam orbit (referred to as a design orbit below) at the maximum energy (referred to as the highest energy below) extracted from the circular accelerator 1, and an orbit 26 represents an example of a beam orbit at the energy lower than the maximum energy. As described above, the orbit of the beam extracted from the circular accelerator 1 is different for each energy. Thus, the strength of a bending magnetic field generated by the first bending magnet 21 and the second bending magnet 22 needs to be controlled in accordance with the energy of the beam extracted from the circular accelerator 1. In addition, the amount by which the first bending magnet 21 and the second bending magnet 22 bend the beam needs to be different for each energy of the beam.

In addition, in the control unit 40a of the control apparatus 40, it is assumed that, when the energy of the extracted beam is the designed maximum energy of the circular accelerator 1, both the first bending magnet 21 and the second bending magnet 22 perform excitation to bend the beam. At this time, preferably, when the energy of the extracted beam is the designed minimum energy of the circular accelerator 1, both the first bending magnet 21 and the second bending magnet 22 perform excitation to bend the beam.

Here, it is assumed that the first bending magnet 21 bends the beam in the outer circumferential direction, the second bending magnet 22 bends the beam in the inner circumferential direction, and the strength of the magnetic field generated by the first bending magnet 21 and the second bending magnet 22 is controlled such that the beam orbit 26 of each energy at the outlet of the second bending magnet 22 coincides with the design orbit 25 when the energy of the beam is the designed maximum value.

Both the design value of the magnetic field strength of the first bending magnet 21 and the design value of the magnetic field strength of the second bending magnet 22 at the maximum energy are not 0, and the design orbit 25 at the maximum energy is curved by the first bending magnet 21 and the second bending magnet 22. In the circular accelerator 1 in the present embodiment, the orbit 26 of the beam having the energy lower than the maximum energy is curved more than the design orbit 25 at the maximum energy. In this manner, the beam orbits in the high energy beam transport 30 are caused to coincide with the design orbit 25 at the maximum energy.

The magnetic field strength of the first bending magnet 21 and the magnetic field strength of the second bending magnet 22 are determined in an adjustment operation (referred to as beam adjustment below) performed before the circular accelerator 1 is used in beam irradiation of particle therapy or the like.

In the case of adjusting the beam orbit 26 at the energy lower than the maximum energy, the control apparatus 40 controls the circular accelerator 1 so that the energy of the beam extracted from the circular accelerator 1 has a target value.

In addition, the control apparatus 40 controls the power supplies 23 and 24, and sets the magnetic field strengths of the first bending magnet 21 and the second bending magnet 22 to design values at the energy to be adjusted. The design values of the magnetic field strengths of the first bending magnet 21 and the second bending magnet 22 are obtained in advance by an analysis of a beam orbit using a computer or the like.

The position and the inclination of the beam in the high energy beam transport 30 are measured using the profile monitors 31 and 32. Since the magnetic field generated by the circular accelerator 1 has a deviation from the design value due to a manufacturing error of the magnetic pole 11 or the like, the position and the inclination of the beam in the high energy beam transport 30 may not completely coincide with the design values in the initial state.

Therefore, in the circular accelerator 1 in the present embodiment, the beam position and the beam inclination are measured by the profile monitors 31 and 32 to measure the deviation from the design values, and the magnetic field strengths of the first bending magnet 21 and the second bending magnet 22 are adjusted such that the beam position and the inclination coincide with the design values.

The deviation of the beam orbit at the extraction port 15 to the inner peripheral side or the outer peripheral side can be obtained by measurement of the profile monitors 31 and 32 in the high energy beam transport 30. Specifically, by obtaining the position and the inclination of the beam in the high energy beam transport 30, it is possible to determine whether the beam orbit at the extraction port 15 is deviated to the inner peripheral side or the outer peripheral side of the design orbit 25.

Since the change amounts in the magnetic field strengths of the first bending magnet 21 and the second bending magnet 22 and the change amounts in the position and the inclination of the beam in the high energy beam transport 30 have a linear relationship, the adjustment amounts in the magnetic field strengths of the first bending magnet 21 and the second bending magnet 22 can be easily obtained from the measurement results of the beam position and the inclination. The change amounts in the magnetic field strengths of the first bending magnet 21 and the second bending magnet 22 may be obtained by the control apparatus 40 based on the measurement results of the beam position and the inclination, or may be separately calculated by an adjuster of the circular accelerator 1 from the measurement results of the beam position and the inclination and input to the control apparatus 40.

After the magnetic field strengths of the first bending magnet 21 and the second bending magnet 22 have been adjusted, the position and the inclination of the beam in the high energy beam transport 30 are measured again, and it is checked that the beam orbit coincides with the design orbit 25 at the maximum energy. At this stage, when there is an unacceptable deviation between the beam orbit and the design orbit 25 at the maximum energy, the magnetic field strengths of the first bending magnet 21 and the second bending magnet 22 are adjusted again in the similar procedure. The adjustment results of the magnetic field strengths are stored in the control apparatus 40. When beam irradiation by the circular accelerator 1 is actually performed, the first bending magnet 21 and the second bending magnet 22 are excited based on the adjustment results.

Next, a method of adjusting the beam orbit at the maximum energy in the circular accelerator 1 in the present embodiment will be described.

In the present embodiment, the adjustment is performed such that the beam orbit 26 at each energy in the high energy beam transport 30 coincides with the design orbit 25 at the highest energy. However, it is expected that even the beam orbit itself at the highest energy is deviated from the design orbit 25 due to an influence of a magnetic field error or the like, it is necessary to adjust the beam orbit for the highest energy as well as other energies.

When the beam orbit at the highest energy in the extraction port 15 is located on the inner peripheral side of the design orbit 25, the beam orbit is bent toward the outer circumferential side by setting the magnetic field strengths of the first bending magnet 21 and the second bending magnet 22 to values higher than the design values, and thus it is possible to cause the beam orbit at the highest energy to coincide with the design orbit 25.

Conversely, when the beam orbit at the highest energy in the extraction port 15 is located on the outer circumferential side of the design orbit 25, it is possible to cause the beam orbit at the highest energy to coincide with the design orbit 25 by setting the magnetic field strengths of the first bending magnet 21 and the second bending magnet 22 to values lower than the design values.

Next, the effect of the present embodiment will be described.

The circular accelerator 1 in the particle therapy system 100 in the first embodiment of the present invention described above is a circular accelerator that accelerates a beam of charged particles circulating in a magnetic field such that a closed orbit for each energy of the beam is eccentric. The circular accelerator 1 includes a beam extraction port for extracting beams of different energies from the closed orbit, a first bending magnet 21 and a second bending magnet 22 that bend the beam extracted from the beam extraction port, and a control unit 40a that controls magnetic field strengths of the first bending magnet and the second bending magnet in accordance with the energy of the extracted beam. When the energy of the extracted beam is a designed maximum energy of the circular accelerator, the control unit 40a excites both the first bending magnet 21 and the second bending magnet 22 to bend the beam. In addition, the diameter of the first bending magnet 21 may be configured to be greater than the diameters of the bending magnets 50a, 50b, and 50c constituting the high energy beam transport 30.

As described above, in the circular accelerator 1 in the present embodiment, the design values of the magnetic field strengths of the first bending magnet 21 and the second bending magnet 22 are set to values other than 0 with respect to the design orbit 25 at the highest energy. Thus, even when the beam orbit at the highest energy in the extraction port 15 is on the outer circumferential side of the design orbit 25, it is possible to cause the beam orbit at the highest energy to coincide with the design orbit 25. As a result, in the circular accelerator 1 in the present embodiment, it is possible to efficiently correct the beam orbit in the high energy beam transport 30, to prevent the expansion of the device constituting the high energy beam transport 30, and to suppress the manufacturing cost of the accelerator system.

In the circular accelerator 1 in the present embodiment, since the closed orbits of the beams having different energies are eccentrically arranged, the beams having different energies can be extracted from the common extraction port 15. As a result, the circular accelerator 1 does not need to install an energy absorber in the high energy beam transport when changing the energy of the irradiation beam. Thus, it is possible to prevent an increase in the irradiation beam size due to scattering with the energy absorber and to perform irradiation with a beam having high quality. Furthermore, in the circular accelerator 1, since it is not necessary to change the strength of the main magnetic field of the circular accelerator 1 in order to change the energy of the extracted beam, it is possible to continuously extract the beam from the circular accelerator 1 and to obtain a high beam current. In particular, it is possible to suppress the expansion of the size of the beam with which the patient 51 is irradiated and to perform irradiation with high accuracy in a scanning irradiation method of three-dimensionally scanning the target volume 52 with the beam. In addition, since the circular accelerator 1 in the present embodiment can perform irradiation with a beam of a large current regardless of the energy of the beam, it is possible to complete the treatment in a shorter time in the particle therapy than in the related art, and to further reduce the burden on the patient.

In the circular accelerator 1 in the present embodiment, the design orbit 25 at the highest energy is curved by the first bending magnet 21 and the second bending magnet 22, that is, the design values of the magnetic field strengths of the bending magnets corresponding to the highest energy are not 0. With this feature, even when the beam orbit before beam adjustment at the maximum energy is located on the outer peripheral side of the design orbit 25, the circular accelerator 1 can correct the beam orbit at the maximum energy and suppress the expansion of the beam passage region in the high energy beam transport 30.

According to the particle therapy system 100 in the present embodiment, it is possible to provide an accelerator system capable of performing irradiation with a beam having a high current and high quality at low cost.

In addition, since the diameter of the second bending magnet 22 is smaller than the diameter of the first bending magnet 21, it is possible to reduce the manufacturing cost.

Furthermore, since the strength of the magnetic field generated by the first bending magnet 21 and the second bending magnet 22 is controlled such that the beam orbit 26 of each energy at the outlet of the second bending magnet 22 coincides with the design orbit 25 when the energy of the beam is the designed maximum value, it is possible to reduce the beam passage region in the high energy beam transport and to reduce the cost of the accelerator system.

The circular accelerator 1 in the present embodiment accelerates the beam of the charged particles circulating in the magnetic field such that the closed orbit of the beam for each energy is eccentric, and extracts the accelerated beam from the closed orbit and guides the beam to the extraction port 15. The beam orbit after being extracted from the extraction port 15 is different depending on the energy of the beam. However, as in the present embodiment, a plurality of bending magnets are installed at positions on the downstream side of the extraction port 15 of the circular accelerator 1 and on the upstream side of the high energy beam transport 30, and the magnetic field strengths of the bending magnets are controlled in accordance with the energy of the beam, so that it is possible to cause the beam orbits to substantially coincide with each other in the high energy beam transport 30. Therefore, it is possible to reduce the size of the particle therapy system. In particular, when the extraction magnetic field generator 13 is configured by a magnetic channel, the magnetic field generated by the magnetic channel is constant. Thus, the beam orbit after extraction from the extraction port 15 is greatly different depending on the energy of the beam, and thus it is possible to obtain the effect of further reducing the size of the particle therapy system.

In the first embodiment, and second and third embodiments described later, the case where the number of bending magnets constituting the orbit control apparatuses 18, 18A, and 18B is two (the first bending magnet and the second bending magnet) has been described. The number of bending magnets installed in the orbit control apparatus provided between the outlet side of the main body of the circular accelerator and the high energy beam transport may be equal to or more than two, and is not particularly limited.

Second Embodiment

Figure 3:
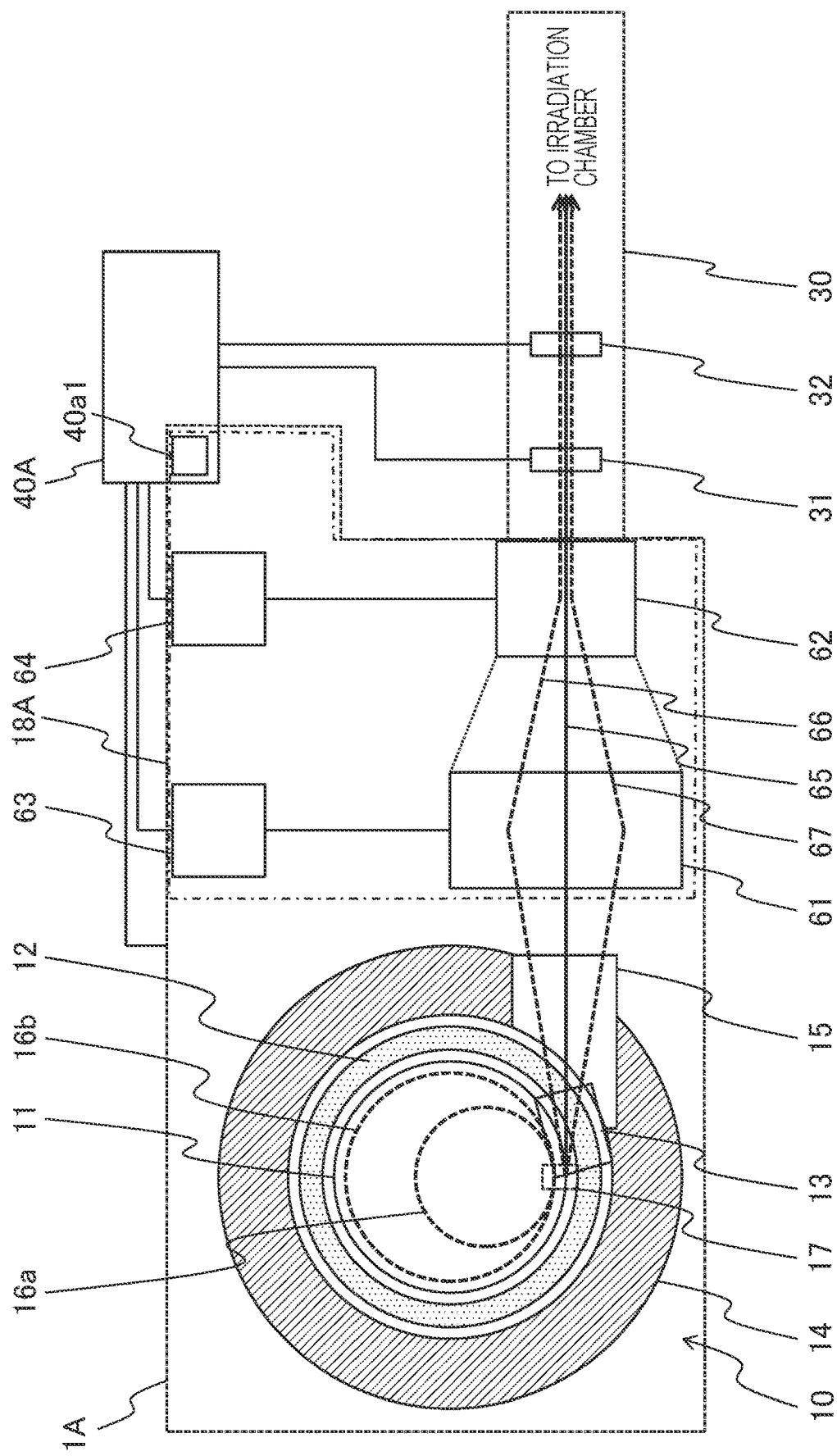
FIG. 3 is a schematic diagram illustrating a configuration of a circular accelerator according to a second embodiment of the present invention.

A circular accelerator and a particle therapy system according to a second embodiment of the present invention will be described with reference to FIG. 3. FIG. 3 is a schematic diagram illustrating a circular accelerator 1A in the present embodiment.

The circular accelerator 1A in the present embodiment illustrated in FIG. 3 basically has the similar configuration to the circular accelerator 1 described in the first embodiment, but the orbit control apparatus 18A in the present embodiment is different from that in the first embodiment in that the orbit control apparatus 18A includes a first bending magnet 61, a second bending magnet 62, power supplies 63 and 64, and a control unit 40*a*1 (preferably, a portion of a control apparatus 40A), and the first bending magnet 61 and the second bending magnet 62 bend a beam in both the outer circumferential direction and the inner circumferential direction of the circular accelerator 1A.

The power supply 63 that excites the first bending magnet 61 and the power supply 64 that excites the second bending magnet 62 are bipolar power supplies capable of switching the direction of a current flowing through a coil constituting the first bending magnet 61 or the second bending magnet 62 in order to bend the beam in both the above directions.

Next, a method of causing the orbits of beams having different energies to coincide with each other in the high energy beam transport 30 by using the first bending magnet 61 and the second bending magnet 62 will be described.

In the present embodiment, the strength of a magnetic field generated by the first bending magnet 61 and the second bending magnet 62 is controlled such that the beam orbit of each energy at the outlet of the second bending magnet 62 coincides with a design orbit 65 when the energy of the beam is larger than the designed minimum value and smaller than the designed maximum value.

For example, the energy serving as a reference (reference energy) is determined between the minimum energy (referred to as the lowest energy below) and the maximum energy extracted from the circular accelerator 1A, and the magnetic field strengths of the first bending magnet 61 and the second bending magnet 62 are controlled such that the beam orbit of each energy in the high energy beam transport 30 coincides with the design orbit 65 at the reference energy.

At this time, the first bending magnet 61 bends a beam (orbit 66) having the lowest energy toward the outer circumferential direction and bends a beam (orbit 67) having the highest energy toward the inner peripheral direction. The second bending magnet 62 bends the beam having the lowest energy in the inner circumferential direction and bends the beam having the highest energy in the outer circumferential direction.

The procedure of adjusting the magnetic field strengths of the first bending magnet 61 and the second bending magnet 62 by using the profile monitors 31 and 32 in the high energy beam transport 30 in the beam adjustment is similar to that in the first embodiment.

Other configurations and operations are substantially the same as those of the circular accelerator 1 and the particle therapy system according to the first embodiment described above, and details thereof will be omitted.

In the circular accelerator 1A and a particle therapy system according to the second embodiment of the present invention, the directions in which the first bending magnet 61 and the second bending magnet 62 bend the beam are different between the lowest energy and the highest energy. Thus, it is possible to efficiently correct a beam orbit in the high energy beam transport 30, similar to the first embodiment. For example, when the beam orbit 67 before adjustment at the highest energy is located on the outer circumferential side of the design orbit 65 at the highest energy, it is possible to cause the beam orbit 67 to coincide with the design orbit 65 by setting the magnetic field strengths of the first bending magnet 61 and the second bending magnet 62 to values smaller than the design values.

In addition, since the power supply 63 that excites the first bending magnet 61 and the power supply 64 that excites the second bending magnet 62 are configured by bipolar power supplies capable of switching the direction of a current flowing through a coil constituting the first bending magnet 61 or the second bending magnet 62, it is possible to further reduce the magnetic field strength of the bending magnet.

Furthermore, the strength of a magnetic field generated by the first bending magnet 61 and the second bending magnet 62 is controlled such that the beam orbit of each energy at the outlet of the second bending magnet 62 coincides with the design orbit 65 when the energy of the beam is larger than the designed minimum value and smaller than the designed maximum value. Thus, in the circular accelerator 1A in the present embodiment, it is only necessary to bend the beam orbit 66 at the lowest energy to the position of the design orbit 65 at the reference energy. Thus, it is possible to reduce the maximum value of the magnetic field strengths of the first bending magnet 61 and the second bending magnet 62 as compared with the first embodiment in which it is necessary to bend the beam to the position of the design orbit 65 at the highest energy. Conversely, even when the maximum value of the magnetic field strengths of the bending magnets is equal to the value in the first embodiment, in the present embodiment, it is possible to shorten the lengths (referred to as a magnetic pole length below) of the first bending magnet 61 and the second bending magnet 62 in the traveling direction and to reduce the size of an accelerator system.

Third Embodiment

A circular accelerator and a particle therapy system according to a third embodiment of the present invention will be described with reference to FIG. 4. FIG. 4 is a schematic diagram illustrating a circular accelerator 1B in the present embodiment.

The circular accelerator 1B in the present embodiment illustrated in FIG. 4 basically has the similar configuration to the circular accelerator 1 described in the first embodiment, but the orbit control apparatus 18B in the present embodiment is different from that in the first embodiment in that the orbit control apparatus 18B includes the first bending magnet 21, a second bending magnet 22B, a quadrupole magnet 71, power supplies 23, 24, and 72, and a control unit 40a2 (preferably, a portion of a control apparatus 40B), and the quadrupole magnet 71 is installed on the downstream side of the first bending magnet 21 and the upstream side of the second bending magnet 22B.

The quadrupole magnet 71 is connected to the power supply 72, and the power supply 72 is connected to the control apparatus 40B. Similar to the first bending magnet 21 and the second bending magnet 22B, the magnetic field strength of the quadrupole magnet 71 is controlled by the control apparatus 40B via the power supply 72.

In the circular accelerator 1B in the present embodiment, a configuration in which the orbit control apparatus 18B includes the quadrupole magnet 71, and the passing beam is converged in the horizontal direction and the vertical direction is made. A beam extracted from the circular accelerator 1B gradually expands in the horizontal direction and the vertical direction. However, by installing the quadrupole magnet 71 as in the present embodiment, it is possible to suppress the expansion of the beam size on the downstream side of the quadrupole magnet 71. This makes it possible to prevent a beam loss caused by collision of the beam with a structure such as the second bending magnet 22B or a vacuum duct. In addition, the circular accelerator 1B in the present embodiment is configured to include the quadrupole magnet 71 on the downstream side of the first bending magnet 21 and on the upstream side of the second bending magnet 22. Thus, it is possible to converge the beam after passing through the first bending magnet 21, in the horizontal direction or the vertical direction by using the quadrupole magnet 71. In addition, the expansion of the beam size in the second bending magnet 22B is suppressed, and it is possible to further reduce the size of the second bending magnet 22B and to reduce the manufacturing cost of the second bending magnet 22B.

In the circular accelerator 1B in the present embodiment, the magnetic field strength of the quadrupole magnet 71, that is, the strength of the generated magnetic field is adjusted in accordance with the energy of the beam.

Other configurations and operations are substantially the same as those of the circular accelerator 1 and the particle therapy system according to the first embodiment described above, and details thereof will be omitted.

Also in the circular accelerator 1B and a particle therapy system according to the third embodiment of the present invention, it is possible to obtain effects substantially similar to those of the circular accelerator 1 and the particle therapy system according to the first embodiment described above.

In the circular accelerator 1B in the present embodiment, since the quadrupole magnet 71 is provided on the upstream side of the second bending magnet 22B, it is possible to reduce the energy dependency of the beam size in the high energy beam transport 30 and to simplify the beam adjustment after the high energy beam transport 30.

In the circular accelerator 1B in the present embodiment, since the quadrupole magnet 71 is installed on the downstream side of the first bending magnet 21, it is ensured that the first bending magnet 21 quickly kicks the beam coming out from the main body 10 of the circular accelerator 1B to bend the beam orbit, and it is possible to suppress an increase in the diameter of the second bending magnet 22B.

In the circular accelerator 1B in the present embodiment, since the strength of the magnetic field generated by the quadrupole magnet 71 is set to a value different for each energy of the beam, it is possible to more reliably obtain the effect of suppressing the expansion of the beam size.

In the circular accelerator 1B in the present embodiment, the configuration in which one quadrupole magnet is installed between the first bending magnet 21 and the second bending magnet 22B has been described as an example, but two or more quadrupole magnets may be installed in this region. When a plurality of quadrupole magnets are installed between the first bending magnet 21 and the second bending magnet 22B, it is possible to further suppress the beam size at the outlet of the second bending magnet 22B as compared with the case where only one quadrupole magnet is installed.

In the present embodiment, the example in which the quadrupole magnet 71 is installed on the downstream side of the first bending magnet 21 has been described. The location at which the quadrupole magnet 71 is installed is not limited thereto, and one or more quadrupole magnets may be installed on the upstream side of the first bending magnet 21.

Further, the quadrupole magnet 71 in the present embodiment is also applicable to the second embodiment. That is, the orbit control apparatus in the second embodiment may be configured to include one or more quadrupole magnets on the upstream side of the second bending magnet 62. Furthermore, preferably, one or more quadrupole magnets may be installed on the downstream side of the first bending magnet 61 in the second embodiment.

Others

The present invention is not limited to the above embodiments, and various modification examples may be provided. The above embodiments are described in detail in order to explain the present invention in an easy-to-understand manner, and the above embodiments are not necessarily limited to a case including all the described configurations.

Further, some components in one embodiment can also be replaced with the components in another embodiment, and the configuration of another embodiment can be added to the configuration of one embodiment. Regarding some components in the embodiments, other components can also be added, deleted, and replaced.

What is claimed is:

1. A circular accelerator that accelerates a beam of charged particles circulating in a magnetic field such that a closed orbit for each energy of the beam is eccentric, the circular accelerator comprising:
    a beam extraction port for extracting beams of different energies from the closed orbit;
    a first bending magnet and a second bending magnet that bend the beam extracted from the beam extraction port; and
    a control unit that controls magnetic field strengths of the first bending magnet and the second bending magnet in accordance with the energy of the extracted beam,
    wherein the control unit excites the first bending magnet and the second bending magnet so that a difference in the orbit of the beam, which varies depending on the energy, is smaller at the position of the second bending magnet than at the position of the first bending magnet, and
    wherein when the energy of the extracted beam is a designed maximum energy of the circular accelerator, the control unit excites both the first bending magnet and the second bending magnet to bend the beam.

2. The circular accelerator according to claim 1,
    wherein when the energy of the extracted beam is a designed minimum energy of the circular accelerator, the control unit excites both the first bending magnet and the second bending magnet to bend the beam.

3. The circular accelerator according to claim 1,
    wherein strength of a magnetic field generated by the first bending magnet and the second bending magnet is controlled such that a beam orbit of each energy at an outlet of the second bending magnet coincides with a design orbit when the energy of the beam is the designed maximum value.

4. The circular accelerator according to claim 1,
    wherein a first power supply that excites the first bending magnet and a second power supply that excites the second bending magnet are configured by bipolar power supplies capable of switching a direction of a current flowing through a coil forming the first bending magnet or the second bending magnet.

5. The circular accelerator according to claim 4,
    wherein strength of a magnetic field generated by the first bending magnet and the second bending magnet is controlled such that a beam orbit of each energy at an outlet of the second bending magnet coincides with a design orbit when the energy of the beam is larger than a designed minimum value and smaller than a designed maximum value.

6. The circular accelerator according to claim 1, further comprising one or more quadrupole magnets installed on an upstream side of the second bending magnet.

7. The circular accelerator according to claim 6,
    wherein the quadrupole magnet is installed on a downstream side of the first bending magnet.

8. The circular accelerator according to claim 6,
    wherein strength of a magnetic field generated by the quadrupole magnet is set to a value different for each energy of the beam.

9. A particle therapy system comprising the circular accelerator according to claim 1.

10. A particle therapy system comprising:
    the circular accelerator according to claim 1;
    a beam transport system that transports the beam extracted from the circular accelerator; and
    an irradiation device that performs irradiation with the beam transported by the beam transport system,
    wherein the beam transport system includes a beam detector that measures a position and an inclination of the passing beam, and
    wherein the control unit controls the magnetic field strengths of the first bending magnet and the second bending magnet such that a beam orbit obtained from the position and the inclination of the beam becomes a designed beam orbit.

* * * * *